United States Patent [19]

Engleman et al.

[11] Patent Number: 4,634,666
[45] Date of Patent: Jan. 6, 1987

[54] HUMAN-MURINE HYBRIDOMA FUSION PARTNER

[75] Inventors: Edgar G. Engleman, Atherton; Steven K. H. Foung, San Francisco; F. Carl Grumet, Stanford, all of Calif.

[73] Assignee: The Board of Trustees of the Leland Stanford Junior University, Stanford, Calif.

[21] Appl. No.: 568,739

[22] Filed: Jan. 6, 1984

[51] Int. Cl.$^4$ .................. C12N 5/00; C12N 15/00
[52] U.S. Cl. ................. 435/68; 435/172.2; 435/240; 435/948; 435/5; 435/7; 424/11; 935/95; 935/96; 935/100; 935/103; 935/106; 935/110; 436/548
[58] Field of Search .................. 260/112 R; 514/1, 2; 424/1.1, 85, 177, 11; 435/4, 5, 7, 68, 70, 172.2, 240, 948, 810; 436/536–542, 510, 548, 808, 811, 815; 935/89, 90, 92, 93, 95, 96, 99, 100, 110, 102–104, 106–108

[56] References Cited

U.S. PATENT DOCUMENTS

| | | | |
|---|---|---|---|
| 4,430,437 | 2/1984 | Hampar et al. | 435/172.2 |
| 4,434,230 | 2/1984 | Ritts, Jr. | 435/240 |
| 4,444,887 | 4/1984 | Hoffman | 435/240 |
| 4,451,570 | 5/1984 | Royston et al. | 435/240 |
| 4,464,465 | 8/1984 | Lostrom | 935/100 |
| 4,472,500 | 9/1984 | Milstein et al. | 435/68 |
| 4,474,893 | 10/1984 | Reading | 435/240 |
| 4,529,694 | 7/1985 | Lazarus et al. | 435/68 |
| 4,574,116 | 3/1986 | Kaplan et al. | 435/68 |

FOREIGN PATENT DOCUMENTS

83/83679 10/1983 PCT Int'l Appl. .
2113715 8/1983 United Kingdom .

OTHER PUBLICATIONS

O'Hare, M. J. et al, *Protides of the Biological Fluids,* vol. 30, pp. 265–268 (1983).
Schlom, J. et al, *Hybridomas in Cancer Diagnosis & Treatment,* Mitchell, M. S. et al, eds., Raven Press, N.Y. (1982), pp. 213–214.
Kozbor, D. et al, *Proc. Natl. Acad. Sci., USA,* vol. 79, pp. 6651–6655 (11-1982).
Erikson, J. et al, *Eur. J. of Immunology,* vol. 12, pp. 697–701 (8-1982).
Edwards, P. A. W. et al, *Eur. J. of Immunology,* vol. 12, pp. 641–648 (8-1982).
Lane, H. C. et al, *J. Exper. Medicine,* vol. 155, pp. 333–338 (1-1982).
Croce, C. M. et al, *Nature,* vol. 288, pp. 488–489 (12-1980).
Nowinski, R. et al, *Science,* vol. 210, pp. 537–539 (10-1980).
Sikora, K. et al, *Blood,* vol. 54(2), pp. 513–518 (8-1979).
Levy, R. et al, *Proc. Natl. Acad. Sci., USA,* vol. 75, pp. 2411–2415 (5-1978).
Houghton, A. N. et al, *J. Exper. Medicine,* vol. 158, pp. 53–65 (7-1983).
Cote, R. J. et al, *Proc. Natl. Acad. Sci., USA,* vol. 80, pp. 2026–2030 (4-1983).
Pickering, J. W. et al, *J. of Immunology,* vol. 129(1), pp. 406–412 (7-1982).
Grose, C. et al, *Infec. Immun.,* vol. 40(1), pp. 381–388 (1983) cited in Biological Abstracts/Biosis 76064917.
Okuno, T. et al, *Virology,* vol. 129(2), pp. 357–368 (1983) cited in Biological Abstracts/Biosis 77032151.
Foung, S. K. H. et al, *J. Immunol. Methods,* vol. 70(1), pp. 83–90 (1984).
Shulman, M. et al, *Nature,* vol. 276, pp. 269–270 (11-1978).
Fazekas de St. Groth, S. et al, *Journal of Immunological Methods,* vol. 35, pp. 1–21 (1980).
Croce, C. M. et al, *European Journal of Immunology,* vol. 10, pp. 486–488 (1980).
Teng, N. N. et al, *Proc. Natl. Acad. Sci., USA,* vol. 80, pp. 7308–7312 (1983).
Kozbor, D. et al, *Human Hybridoma and Monoclonal Antibodies,* Engleman, E. G. et al, eds., Plenum Press (1985), pp. 21–36.
Teng, N. N. H. et al, *Human Hybridomas and Monoclonal Antibodies,* Engleman, E. G. et al, eds., Plenum Press (1985), pp. 71–91.
Foung, S. K. H. et al, *Human Hybridomas and Monoclonal Antibodies,* Engleman, E. G. et al, eds., Plenum Press (1985), pp. 135–148.
Foung, S. K. H. et al, *Vox Sang.,* 16 FR preprint.
Ostberg, L. et al, *Hybridoma* 2(4): 361–367 (1983).
Foung, S. K. H. et al, *Journal of Infectious Diseases,* 152(2): 280–285 (1985).

*Primary Examiner*—Charles F. Warren
*Assistant Examiner*—Margaret Moskowitz
*Attorney, Agent, or Firm*—Ciotti & Murashige

[57] ABSTRACT

By careful screening and mutation, a human-murine hybridoma suitable as a fusion partner for immortalizing an antibody-secreting B cell has been generated. The trioma fusion products of this immortalizing partner are stable producers of human monoclonal antibodies. A trioma which produces monoclonal human anti-varicella zoster is disclosed.

14 Claims, No Drawings much lower than  rights in this invention.

HUMAN-MURINE HYBRIDOMA FUSION PARTNER

This invention was made with Government support under HL 29572 awarded by the National Institutes of Health. The Government has certain rights in this invention.

BACKGROUND

The field of the present invention is the production of human monoclonal antibodies through fused hybrid cells. In particular, the present invention relates to novel trioma producers of human monoclonal antibodies and to murine-human hybridoma immortalizing cell lines suitable for their preparation.

Human antibodies have been used both for diagnostic and therapeutic purposes for a number of years. Diagnostic techniques include blood typing for transfusion (Yankee, R. A., et al, *New Eng. J. Med.*, 281:1208 (1969)); or transplantation (Grumet, F. C., et al, *Hum. Immunol*, 5:61 (1982)). Therapeutic applications include prophylaxis of Rh hemolytic disease, (Nusbacher, T., et al., *New Eng. J. Med.*, 303: 935 (1980); and injection of anti-varicella zoster plasma (Grose, C., *Human Herpes Virus Inf.* (1982) Marcel Delcker, N.Y.). The oldest technique for obtaining these antibodies is isolation from immune serum. However, the small concentration of the antibody of desired specificity among those which are generally present in serum presents a serious drawback.

More recently, the production of human monoclonal antibodies has become possible and these may serve as tools in diagnostic testing and in therapy. Two major approaches for the production of human monoclonal antibodies (Mab's) have been used: direct immortalization of immunized lymphocytes with Epstein-Barr Virus (EBV) and Mab production by hybridomas formed between immortalized human B cell lines (EBV), lymphoblastoid, or human or murine myelomas, and human B lymphocytes from an immunized host. Neither of these approaches has proved entirely satisfactory.

It is common experience among practitioners in the art that EBV transformation, while successful in forming Mab-secreting cultures, will often fail to provide antigen specific EBV transformed cells which have sufficiently long life spans to provide reliable sources of the desired antibodies (Kozbor, D., et al, *Hybridoma*, 1:323 (1982). Thus, this method fails to provide reliably for antibody production over extended periods. Previously produced hybridomas between immunized human B cells and appropriately drug marked mouse or human myeloma or human lymphoblastoid cell lines have suffered from low frequency of hybrid formation in the case of human-human hybridizations (Olsson, L., et al., *Proc Nat Acad Sci*, 212:767 (1980)) or chromosomal instability in the case of murine-human hybridomas (Nowinski, R., et al., *Science* 210:537 (1980), Lane, H. C., et al, *J Exp Med*, 155:333 (1982)). (Murine-murine hybridomas are stable, but the antibodies produced are immunogenic if used in passive therapy.)

An immunized experimental animal can sometimes serve as a source for specific antibody-secreting B cells to provide the immunized lymphoid member of the hybridoma. This method cannot be used, however, to provide reagents for HLA or other blood type testing since when human antigens are injected, the plethora of antibodies elicited is mostly immunoreactive to antigens common to all humans, and the desired antigen-specific antibody is formed only as a very small percentage of the total response. Further, these non-human antibodies can themselves result in an adverse immune response if injected for human therapy.

The problems associated with human monoclonal antibody production have been greatly ameliorated by the immortalizing hybridoma and resultant triomas of the present invention. The present invention, thus, provides a means for producing human antibodies of the desired specificity dependably and over long periods of time, using a stable, immortal Mab producing source.

SUMMARY OF THE INVENTION

The invention, in one important aspect, provides an ideal fusion partner for specific B-lymphoid cell lines, producing triomas that secrete specific antibodies of human character.

These "immortalizing" hybridomas of the invention are extraordinarily stable and retain sufficient human character that when fused with immunized human lymphoid cells, form triomas which have the capacity to secrete human antibody. The monoclonal antibodies produced are of human character and should be of low immunogenicity when used in therapeutic applications. Furthermore, the immortalizing hybridoma also appears to confer stability on the resulting daughter hybrid with respect to its ability to produce the desired antibody.

Thus, this aspect of the invention concerns an immortalizing, non-secreting hybridoma having human characteristics. It is prepared by fusing mouse myeloma cells with human B lymphocytes and selecting the fusion product for stable immunoglobulin secretion and HLA surface antigen production, followed by treating the selected fusion product with mutagen and selecting the mutated product for non-secretion of immunoglobulin but retention of HLA antigen production. A particular embodiment of such an immortalizing hybridoma has been designated SBC-H20 and deposited at the ATCC on or about Dec. 13, 1983, and has the American Type Culture Collection (ATCC), 12301 Parklawn Drive, Rockville, MD 20852# HB 8464.

In a second aspect, the present invention relates to the products of fusing the immortalizing hybridomas with suitable human immunized lymphoid cells. These "triomas" have the enhanced stability above referred to, and are useful sources of desired Mab's. A specific embodiment of such triomas secretes antivaricella zoster virus antibody. This trioma was deposited on or about Dec. 13, 1983, and given the ATCC #HB 8463. The invention also relates to methods of producing such triomas and of utilizing them for antibody production.

In still other aspects, the invention relates to the human monoclonal antibodies which are produced by the triomas of the invention and to their diagnostic and therapeutic compositions and uses.

DETAILED DESCRIPTION

A. Definitions

As used herein, "trioma" refers to a cell line which contains genetic components originating in three originally separate cell linages. As used in the context of the invention, these triomas are stable, immortalized antibody producers which result from the fusion of a human-murine hybridoma with a human antibody producing B cell.

The human-murine hybridoma (the "immortalizing hybridoma") is an immortal cell line which results from the fusion of a murine myeloma or other murine tumor cell with human lymphoids derived from a normal (preferably non-immunized) subject. As described in detail below, by careful selection and mutation, an immortalizing hybridoma which provides improved chromosomal stability, has human characteristics, and which does not secrete immunoglobulin is obtained. The antibody secreting capacity of the trioma is provided by the third member of the fusion which is typically derived either from B cells of an immunized human individual, or with such B cells altered so that they, too, are immortal.

"Non-secreting" hybridoma refers to a hybridoma which is capable of continuous reproduction and, therefore, is immortal, which lacks the capacity to secrete immunoglobulin.

A hybridoma "having human characteristics" refers to a hybridoma which retains detectable human-derived chromosomes such as those producing human HLA antigen which will be expressed on the cell surface.

Lymphoid cells "immunized against a predefined determinant" refers to lymph cells derived from an individual who has been exposed to an antigen having the determinant of choice. Thus, for example, an individual can be induced to produce from its lymphoid B cells antibodies against the antigenic determinants of various blood types, by virtue of exposure, through transfusions or previous pregnancy, or against the antigenic determinants of specific viruses or of bacteria by virtue of exposure through past infections or vaccinations. B cells which produce such antibodies are defined by this term.

"Functional equivalent" is intended to mean a human monoclonal antibody other than the specific exemplified human immunoglobulin that also is specific to the referenced antigen, e.g. immunoreactive with varicella zoster specifically, in the case of the Mab of the invention. Preferred functional equivalents recognize the same determinant the antigen and cross-block the exemplified monoclonal antibody.

"Cell line" refers to various embodiments including but not limited to individual cells, harvested cells and cultures containing cells so long as these are derived from cells of the cell line referred to. By "derived" is meant progeny or issue. It is, further, known in the art that spontaneous or induced changes can take place in karyotype during storage or transfer. Therefore, cells derived from the cell line referred to may not be precisely identical to the ancestral cells or cultures, and any cell line referred to includes such variants.

B. General Method

The non-secreting, characteristically human hybridomas of the present invention are prepared by fusing murine myeloma cells with human peripheral B lymphocytes derived from peripheral blood, spleen or lymph nodes of human donors, followed by careful selection for clones and by mutagenesis. The resultants are suitable for subsequent fusion with antibody-producing lymphocytes. Fusions are carried out using standard conditions known in the art, such as, for example, incubation in the presence of polyethylene glycol, followed by selection for the desired fusion products. In the context of the present invention, the selection process is important, particularly with regard to the immortalizing hybridomas which must be carefully cloned by limiting dilution and screened to assure the recovery of a cell line with the desired characteristics.

B.1. Component Cell Lines

B.1.a. For Immortalizing Hybridomas of the Invention.

Fusion partners which make up the immortalizing hybridomas are murine myeloma cells and human lymphoid B cells. Murine myeloma cell lines are commonly available and may be obtained through the ATCC. Human lymphoid B cells are isolated from the plasma of normal individuals using conventional techniques. Such procedures include density gradient purification and separation of B cells from T cells using standard sheep erythrocyte rosetting techniques known in the art.

B.1.b. For Mab-Producing Triomas

The immortalizing partner of the trioma is, of course, the hybridoma of the present invention, preparation of which is described in detail hereinbelow. The antibody-producing component can be prepared using standard techniques from a choice of sources dependent on the antigen which the Mab is desired to recognize. Where an immunocomplexing reaction against a determinant associated with an infectious agent such as virus or bacterium is desired, plasma from an individual having had an infection with this agent is one source of these antibodies. Animal sources may also be produced in this case after deliberate innoculation to produce infections. Such non-human origins are not as desirable for therapeutic applications since the resulting antibodies, though produced by the method of the invention, retain non-human character and therefore may be somewhat immunogenic. For diagnostic applications, however, this is not a serious drawback.

When it is required to obtain antibodies reacting against normal human antigens such as, for example, the blood type antigens A or B or the characteristic HLA antigens exhibited by particular individuals, normal donors having the appropriate antibodies by virtue of transfusion or pregnancy are required. Ordinarily, the source of such cells would be peripheral blood; however, if available, spleen cells or lymph node cells are a second source of these antibody-producing cells. Separation and isolation techniques are described above.

The antibody producer may also be prepared by in vivo transformation of the appropriate B-lymphocytes with an infectious virus so that they are immortalized. Typical of such techniques is that described for transformation with Epstein-Barr virus (EBV) by Sly, W. S., et al, *Tissue Antigens,* 7:165 (1976).

While the monoclonal antibodies that are specifically exemplified herein are a human IgM which is an anti-red blood cell and a human IgG1 which is antivaricella zoster, the invention is not limited to any particular species, class, or subclass of immunoglobulin. Other specific monoclonal antibodies may be other members of the IgG subclasses such as IgG1, IgG2, IgG3, etc., or other members of the IgM class. The members of the remaining immunoglobulin classes IgA, IgE or IgD can also be produced by trioma fusion products of the murine-human, non-secreting hybridoma and identified by following the screening procedures described herein.

B.2. Fusion Procedure

Fusions to form the murine-human non-secreting hybridomas and the triomas of the inventions as exemplified are performed basically by the method of Kohler and Milstein, *Nature,* 256:495 (1975). Briefly, a tumor cell line (to make the hybridomas) or hybridoma (to make the triomas) is combined with partner cells (typically spleen cells or B lymphocytes) that produce the antibody of interest using a fusogen such as polyethylene glycol under suitable conditions—typically 40%–50% polyethylene glycol, of MW 1000 to 4000 at room temperature to 40°, preferably about 37°. Fusion requires about 5–10 minutes, and the cells are then centrifuged and screened.

B.3. Screening Procedure

After any fusion procedure, screening for cells which are, indeed, hybridized products is made by culturing cells centrifuged from the fusion medium in growth medium which is selective for the desired hybrids. Ordinarily, non-immortalized fusion partners cannot survive repeated transfers on any medium, and hence will not survive repeated culturing of the centrifuged cells. Commonly used lines of immortalized murine myeloma cells, however, are incapable of growth on certain selective media which have been chosen to deprive them of their ability to synthesize DNA. Two very commonly used media of this description are "hypoxanthine-aminopterin-thymidine" or "HAT" medium and azaserine-hypoxanthine medium or "AH" medium. Both of these selection media take advantage of the capacity of the normal cells to utilize a "salvage" pathway for DNA synthesis under circumstances where the de novo process is inhibited. This salvage process, which requires hypoxanthine phosphoribosyl transferase (HPRT) is generally inoperable in these commonly used murine myeloma cells (although they retain the de novo pathway). Thus, both normal cells and the hybrids (which acquire the normal cells' ability to synthesize HPRT) can grow in medium containing hypoxanthine even if the de novo synthesis of DNA is inhibited by the medium; tumor cells cannot. Aminopterin in the HAT medium, and azaserine in the AH medium are both inhibitors of the de novo DNA synthesis pathway. (Aminopterin inhibits both purine and pyrimidine nucleotide synthesis and thus thymidine is required as well as hypoxanthine for the salvage pathway. Azaserine inhibits only purine synthesis, so only hypoxanthine for the salvage pathway is required.)

In short, only hybridized cells can both survive repeated transfers and grow in HAT or AH medium—normal cells cannot survive because they are not immortalized and do not survive repeated transfers; unhybridized tumor cells cannot survive because they lack the salvage pathway which permits the use of hypoxanthine to overcome ammopterin or azaserine inhibition.

Successful fusions are first produced by using AH or HAT medium, but additional selection procedures are required. This is accomplished in part by limiting dilution and individual clone analysis.

In those special instances where the immortalized hybridoma is to be fused to a transformed antibody producer, an additional property is required. The transformed antibody producer does not die from multiple transfers as would a normal cell and unlike the common murine myeloma immortalizing lines is not sensitive to HAT or AH medium. Thus, these usual selection means will permit such unfused, transformed lymphocytes to survive. A screening procedure for successful triomas thus requires inclusion in the medium of a drug to which these transformed parent cells are sensitive. Therefore, the immortalizing hybridoma must, in addition to other desired properties, have acquired resistance to this drug so that it can transfer resistance to the trioma. In the example below, the drug is ouabain.

As mentioned above, the selection procedure employed in selecting the immortalizing hybridomas of the invention goes far beyond simple selection for successfully hybridized murine-human hybridomas. Additional properties in the cell line, are required and must be selected for or imparted by mutagenesis. These immortalizing hybridomas must show stable human characteristics, non-secretion of immunoglobulin, sensitivity to a medium to which the fusion partner will be resistant, and if an immortalized lymphoid partner is used, resistance to a drug capable of destroying the fusion partner. This particular collection of characteristics requires a unique and well-designed screening and mutagenesis process.

Briefly, the cells centrifuged from the fusion mixture are diluted and plated in microtiter plates or other convenient means for growing large numbers of single colonies. Screening is done using AH or HAT medium growth. Selection from successful colonies is made on the basis of assay procedures related to stability and human character. Thus, from among the many colonies assayed, several are chosen which continue to produce immunoglobulin in the supernatant fluid for a suitable period of time, preferably in excess of six months (one criterion for stability). The continued production of such immunoglobulin indicates that the characteristics conferred by the lymphocyte partner have not been lost (lymphocytes which were unfused will, of course, not survive). Retention of human characteristics was assessed by assaying the cell surfaces for the presence of HLA antigen. The selected colonies continue to exhibit HLA antigen production at their cell surfaces (another indication of stability, as well as human character).

The selected clones, are then subjected to a mutagen such as 6-thioguanine in order to destroy their ability to secrete immunoglobulin and confer HAT or AH sensitivity, and ouabain resistance. This will clear the way for later fusion to give a trioma, and subsequent use of the fusion product to secrete a particular monoclonal antibody characteristic of the added fusion partner. Accordingly, the selected cell lines are grown in the presence of a mutagen such as 6-thioguanine in increasing concentrations, and mutants selected for inability further to secrete immunoglobulin, HAT/AH sensitivity and ouabain resistance. However, only those colonies which remain capable of surface HLA antigen expression are chosen.

In summary, the immortalizing hybridoma which is central to the invention herein, is derived on the basis of a very careful selection/mutagenesis procedure from its human-murine parents. The initial selection is based on HAT/AH sensitivity, Ig secretion, and HLA surface antigen production. Mutation causes loss of endogenous Ig secretion and restores AH/HAT sensitivity, but HLA production is retained.

B.4 Production and Purification of Human Monoclonal Antibodies From Cultured Cells After fusion with an antibody-producing human lymphoid cell in accordance with the procedures set forth above, the immortalizing hybridomas of the invention are converted to trioma producers of the specific antibody brought to the union by the new partner.

The resulting triomas are selected by using an appropriate selection medium. If the antibody-producing partner is a normal cell line, selection medium can simply be the HAT or AH medium which will discriminate against unfused immortalizing hybridoma cells—the antibody producer fails to maintain immortality in successive transfers. If the antibody producer is itself an immortalized cell—i.e. for example, a virus transformed lymphocyte, an additional selection in the presence of, for example, ouabain to kill these unhybridized cells is also required. Alternative selection procedures are, of course, possible depending on the nature of the cells used in the fusion. It would, for example, be possible to confer by mutagenesis alternate sensitivities on the immortalizing hybridoma which would respond to other medium selecting factors besides HAT and AH.

Clones having the required specificity are identified by assaying the trioma culture medium for the ability to bind to the desired antigen and the nature of the Mabs may be further characterized by testing for specificity. Triomas that produce human antibodies having the desired specificity may be subcloned by limiting dilution techniques and grown in vitro in culture medium or injected into selected host animals and grown in vivo.

The antibodies may be separated from resulting culture medium or body fluids by conventional antibody fractionation procedures such as ammonium sulfate precipitation, DEAE cellulose chromatography, affinity chromatrography and the like.

B.5 Use of Mab Produced By the Method of the Invention As A Diagnostic

If desired, the human monoclonal antibodies may be derivatized (labeled) using conventional labeling reagents and procedures. As used herein, the term "label" is intended to include both moieties that may be detected directly, such as radioisotopes or fluorochromes, and reactive moieties that are detected indirectly via a reaction that forms a detectable product, such as enzymes that are reacted with substrate to form a product that may be detected spectrophotometrically.

The use of Mab in detecting a desired antigen is substantially an immunoassay, and a variety of conventional immunoassay procedures such as ELISA or RIA may be used. If the antigen is already immobilized on a solid insoluble support, the antibody may be applied to the support, incubated under conditions that allow immune complex formation between the antibody and any immobilized antigen on the support, and the support washed to removed unbound antibody. Temperature, pH, and duration are the most important conditions in the incubation. The temperature will usually range between 5° C. and 40° C., the pH will usually range between 6 and 9 and the binding reaction will usually reach equilibrium in about 1 to 18 hr. Antibody will normally be used in excess.

In instances where the antibody is labeled directly, immune complexes may be detected via the label, e.g. radioactive or fluorescent on the antibody. A more common and preferred procedure is to use unlabeled monoclonal antibody and incubate the desired antigen-monoclonal antibody complex with an enzyme-conjugated antibody against the monoclonal antibody. The same incubation conditions as were used in the initial incubation may be used. The resulting ternary complex may be treated with substrate and detected spectrophotometrically via an enzyme-substrate reaction. By using conventional procedures in which the detection means is bound indirectly to the antigen-monoclonal antibody via one or more layers of immunochemical, it may be possible to amplify the detection signal to improve the sensitivity or the detection limit of the procedure.

Kits for carrying out the above described tests will normally contain an antigen immobilizing material, the monoclonal antibody, enzyme-conjugated antibody against the monoclonal antibody and an appropriate substrate. The kits may also contain a suitable buffer for dilution and washing, a post-coating preparation such as bovine serum albumin and directions for carrying out the tests. These components may be packaged and stored in conventional manners.

B.6 Use of the Mabs of the Invention in Purifying Antigen

The antibodies may also be covalently coupled to chromatography supports (e.g., the surfaces of tubes or plates or the surface of particulate bodies such as beads) using available bifunctional coupling agents, such as carbodiimides, to make effective adsorbents for affinity purifying a desired antigen. A solution of the antigen in cold buffer at pH 7–7.5 is passed through a column containing the monoclonal antibody fixed to a support. The desired antigen will be retained by the column and may be eluted therefrom with an appropriate elutant.

Kits for isolating the desired antigen will contain the monoclonal antibody conjugated to the support, buffer to serve as a medium for adsorbing the antigen to the support and an elution reagent.

B.7 Use of the Mabs of the Invention in Therapy

The use of Mab's in therapy has been limited due to the difficulty of providing a stable source of human monoclonal antibodies. However, the method based on the invention is similar to that presently employed using polyclonal sources. A particularly well known application is the use of gamma globulin to prevent infection. References to the use of immune plasma in immunocompromised patients for prevention of varicellazoster infection, and for prevention of Rh hemolytic disease in the newborn have been cited above. Briefly, the antibody is injected in a plasma-compatible solution in amounts determined by the needs of the subject.

C. EXAMPLES

The following examples serve to illustrate the invention and are not intended to limit its scope. While the fusion partners for combination with the immortalizing hybridoma of the invention have led to the production of human anti-red blood cell type A and human anti-varicella monoclonal antibodies, by a suitable alternate selection of the secreting B cell, a variety of monoclonal antibodies may be produced, such as, for instance, antibodies against *E. coli*, cytomegalovirus (CMV), hepatitis (HBV) or other infective agents and against red blood cell type B and against HLA antigens. Further, in producing the immortalizing hybridoma, B cells from a normal particular individual have been used, of course, any normal B lymphocytes can be utilized as the fusion partner with mouse myeloma.

C.1 Preparation of SBC-H20; An Immortalizing Hybridoma

Mouse myeloma cell line SP2/08A2 was obtained for use as the immortalizing partner from Frank Fitch, University of Chicago. This cell line is freely available and can be used without restriction. Other mouse myeloma lines are also readily available. Human peripheral B lymphocytes were isolated from the heparinized plasma of a normal human donor by Ficoll-Hypaque gradient as described by Boyum, A., *Scand J Lab Clin Invent* 21: (Suppl. 97) 77 (1968). The peripheral B lymphocytes B and myeloma cells were mixed at a 1:1 ratio, washed once in RPMI 1640 medium (Gibco), and pelleted at 250×g for 10 minutes. The pellet was gently resuspended in 1 ml of RPMI with 40–45% (volume/volume) polyethylene glycol solution, MW 1430–1570 (BDH Chemicals, Poole, England) which was prewarmed to 37° C. After two minutes at room temperature, the cell suspension was diluted to 6 ml with RPMI, centrifuged at 500×g for 3 minutes, and, beginning 8 minutes from the onset of fusion, the cell pellet washed with RPMI containing 10% fetal calf serum. The pelleted cells were plated in multi-well trays using suitable dilutions to obtain individual clones. The colonies were grown on AH selection medium containing 2 µg/ml azaserine and 100 µM hypoxanthine, and successful clones were assayed for immunoglobulin production and for HLA surface proteins using the assay methods as set forth in paragraphs C.8.a and C.8.b herein.

A hybrid clone which had had a stable immunoglobulin production for 6 months, and which was consistently producing HLA surface protein was selected.

This clone was then placed in Iscove's medium (IDMEM) (Gibco) containing 10% fetal calf serum, 2 mM glutamine, 100 units penicillin, 100 mg streptomycin per ml, as well as the mutagen $2\times10^{-6}M$ thioguanine (Sigma). The concentration of 6-thioguanine was progressively increased to $2\times10^{-5}M$ over a period of approximately 30 days. The resulting mutant hybrids were sub-cloned, and the colonies tested for immunoglobulin secretion. A non-secreting sub-line which was HAT/AH sensitive, resistant to $10^{-6}$ M ouabain, and which retained ability to produce HLA surface antigen, was designated SBC-H20. A sample of this cell line was deposited with ATCC on Dec. 13, 1983, and given the designation ATCC HB 8464. The characteristics of this murine-human hybridoma include: sensitivity to HAT and AH media, resistance to ouabain (Sigma) to a concentration of $10^{-6}M$, non-secretion of immunoglobulins, human chromosomal stability over time, and production of HLA surface protein.

C.2 Preparation of Anti-A Secreting EBV Transformed Lymphocytes

Lymphocytes were isolated from a spleen removed from a type 0 individual (who required splenectomy because of a severe hemolytic anemia) by separation on a Ficoll-Hypaque density gradient of specific gravity 1.077 according to the procedure of Boyum, A. (supra). The cells were cultured at a cell concentration of $2\times10^6$/ml in IDMEM containing 15% fetal calf serum and 0.03% type Al red blood cells. After three days, T cells were removed by the single step rosetting method of Saxon, A., et al, *J Immunol Methods*, 12:285 (1976) using 2-aminoethylesothiouronium bromide hydrobromide, and the residual B cells were transformed by the EBV containing supernatant from the marmoset line B-958 according to the procedure of Sly, et al (supra). The cells from the transforming mixture were transferred to microtiter plates at a concentration of $10^5$ cells per well and cultured for 14 days in IDMEM with 15% FCS medium. The cells were then assayed for human anti A type red blood cell antibody by the method of hemagglutination, and positive wells expanded and cloned in soft agar using human fibroblast feeder. The sub-clones were then isolated and again assayed for anti-A activity by the foregoing method. Clones testing positive against human A red blood cells were then expanded in liquid medium culture.

C.3 Preparation of Anti-Human Al Secreting Triomas

Triomas producing anti-human A antibodies were prepared using the fusion procedures set forth in paragraph C.1 except using a 1:10 mixture of the anti-A lymphocytes prepared in paragraph C.2 to SBC-H20 cells (or SP2/08A2 cells as a control). After washing in RPMI with 10% fetal calf serum, the cells were plated in microtiter plates at a density of $1\times10^6$ cells per well over irradiated mouse spleen feeder cells and grown under a humidified 6% $CO_2$ atmosphere at 37° C. Two similar selection media were used; HAT selection medium containing 100 µM hypoxanthine, 50 nM aminopterin, 15 µM thymidine, as well as 0.1 mM ouabain and AH selection medium containing 2 µg/ml azaserine, 100 µM hypoxanthine and 0.1 µM ouabain. Unfused SBC-H20 and unfused EBV transformed anti-A lymphocytes of paragraph C.2 were dead after 10 days. The resulting fused cells were further selected for 10 days using 0.1 µM ouabain and for 14 days by HAT or AH (supra). Individual clones were verified by sequential soft agar and limiting dilution cloning.

C.4 Verification of Trioma Anti-A Forming Clones By Chromosomal Analysis

Chromosome preparations were obtained from the trioma clones of paragraph C.3 and assessed to verify successful fusions.

Chromosome preparations were made as follows: Approximately $10^6$ cells per ml were placed in basic growth medium containing vinblastine at 0.5 µg per ml (Lilly), incubated for 3 hours, and centrifuged at 250×g for 10 minutes. The cell pellet was resuspended in 5 ml of hypotonic solution (growth medium/distilled water, 1:4) for 10 minutes and the cells repelleted, washed twice in fixative comprising methanol:glacial acetic acid, 5:1, and finally resuspended in a few drops of fixative. The suspensions were air dried on microscope slides, stained with Giemsa (Sigma) and examined microscopically.

The triomas were thus shown to contain 100–110 chromosomes, of which 70–75 have acrocentric centromeres suggestive of murine origin, and the rest of which have metacentric centromeres, suggestive of human origin. (The parent SBC-H20 cells have 75–80 chromosomes; 3 with metracentric centromeres.)

C.5 Anti-Human Al Antibody Production by Trioma

Supernatants of several of the cell lines prepared in paragraph C.3 were tested for specific antibody production against types Al and B red blood cells using an agglutination assay. A positive result was defined using V bottom microtiter trays (Falcon Lab) and assuming macroscopic agglutination according to the method of Parker, J. et al, *Transfusion*, 18:417 (1978) after addition of test solution and centrifugation at 250 ×g for 45 seconds. Quantitation was achieved by testing serial doubling dilutions with 3% bovine serum albumin in normal saline the end point being defined as the limiting dilution.

The results are shown in Table 1.

TABLE 1

Frequency and Titer of Hybridomas Secreting Human Anti-A Antibody*

| | Number of Wells with Anti-A Activity | Titer** |
|---|---|---|
| Secreting Line | | |
| EBV line | | 1:2,000 |
| SP2/anti A hybrids | | |
| Parents | 19/22 | 1:32 |
| Clones | 0/23 | 0 |
| Triomas | | |
| SBC-H20/anti-A hybrids | | |
| Parents | 29/31 | 1:8,192 |
| Clones | 13/21 | 1:16,384 |
| Subclones | 36/53 | 1:32,768 |

*All antigen specific IgM with kappa light chain
**Maximum dilution permitting detection of agglutination The superiority of the SBC-H20 as a fusion partner to obtain a stable antibody secreting line is shown by these results. While fusion of the EBV line with the murine SP2 anti-A secreters, the titer was several hundred fold less than the fusion with SBC-H20, and the secretion capability was lost after one transfer. The triomas, on the other hand, maintained (and increased titer) secretion capability after at least two transfers.

The triomas formed by fusion with SBC-H20 were capable of secreting monoclonal anti-A at titers at least four fold higher than the parent EBV transformed lymphocytes themselves through seveal transfers, and for a period of more than 8 months. The amounts produced are more than 10 μg/ml; comparable to the level of production by a typical murine-murine hybridoma. The quantity produced by the unhybridized EBV transformed cell line, however, was approximately 10 fold less. The specificity of this immunoglobulin is shown in Table 2. Supernatants were tested using the agglutination assay against 173 donor derived red blood cell preparations which were classified as the groups shown.

TABLE 2

Reactivity of Human Monoclonal Anti-A Antibody Against Random Donor Cells

| Positively Testing Cells | Number Tested | % Positive |
|---|---|---|
| A2 | 13 | 100 |
| A1 | 59 | 100 |
| A1B | 4 | 100 |
| A2B | 1 | 100 |
| Aint | 7 | 100 |
| B | 16 | 0 |
| O | 71 | 0 |

The succeeding paragraphs C.6 and C.7 describe the preparation of human antibodies against Varicella Zoster Virus (VZV) for potential diagnostic or therapeutic use. While the disease caused by VZV is commonly trivial (chicken- pox or herpes zoster), it can be serious in an immunocompromised host. The human monoclonal antibodies, whose preparation is described below, can be used for therapy in such hosts by parenteral administration to the subject.

C.6 Preparation of Triomas Secreting Antibody Against Varicella Zoster Virus (VZV)

The triomas secreting anti-VZV were prepared by fusion of the SBC-H20 cell line, whose preparation is described in paragraph C.1, with lymphocytes isolated from the peripheral blood of a donor with acute varicella infection but who is otherwise normal. The blood lymphocytes were separated using the methods described in paragraph C.2. T cells were removed by rosetting, Saxon (supra), and the isolated B lymphocytes used for fusion herein. The fusion procedure was exactly as described in paragraph C.1 except that IDMEM medium was used instead of RPMI and the cells transferred to microtiter plates at $10^5$ cells/well over irradiated spleen feeder cells in HAT selection medium (as described in paragraph C.3); except that the addition of ouabain is not required as the lymphocytes are untransformed. Hybridoma growth was observed in 37 or 58 seeded wells after 2 weeks and HAT selection was continued for 3 weeks. Monoclonality was verified by sequential limiting dilution cloning, using microtiter plates. Thus, 50% of the hybrids were secreting anti-VZV, as assayed by the method of paragraph C.8.c below.

Several wells were cloned at 0.5 cells per well; clones from two different parent wells showed positive reactivity in the RIA anti-VZV assay of paragraph C.8.c. some of these were again subcloned, and at least two of the subclones assayed from both patent wells showed anti-VZV IgG levels $>10$ μg/$10^6$ cells/24 hours as determined by ELISA, and in the viral plaque reduction assay of paragraph C.8.d, showed neutralization at 5 μg/ml of protein. One of these subclones was designated SBC-H21, deposited at ATCC on December 13, 1983, and given ATCC #HB 8463.

C.7. Characterization of Mab Secreted by the Trioma

Multiple hybrid clones secreting anti-VZV antibodies have been obtained by soft agar and limiting dilution techniques. The viral specific antibody of one of the clones has been further characterized. Several of the clones secrete different antibodies specific for distinct viral epitopes since the clones were derived from multiple hybrid parents and some produce antibody with lambda and others with kappa light chains as determined by enzyme-linked immunoassay. All secreting subclones have produced antigen-specific IgG for greater than eight months after the initial fusion.

C.8 Assays

The following paragraphs set forth assay procedures useful in the illustrations of the Invention.

C.8.a. Assay for Immunoglobulin Secretion.

Where it was desirable for general or class specific immunoglobulin production to be assessed, immunoglobulin content in the supernatant was determined by enzyme linked immunoassay. Affinity purified, class specific goat anti-human immunoglobulin for example (IgG (Tago, Burlingame, Calif.) is adsorbed onto each well of a flexible flat-bottom microtiter tray (Dynatech Laboratory, Alexandria, Va.) for 5 hours, and then left overnight at 4° C. After aspiration of the coating each well is incubated in 5% bovine serum albumin (BSA) in phosphate buffered saline (PBS) for an hour at 37° C. After washing with 3x cold PBS and air drying, 25 lambda of hybridoma or trioma supernatant or, as a control, a known amount of purified human IgG is added, and the trays incubated overnight at 4° C. After again washing 3× with cold PBS and air drying, 100 lambda of dilute alkaline phosphatase conjugated goat albumin IgG heavy chain specific antibody (Tago) was added to each well (1:100 dilution) and the plates incubated for 1 hour at 4° C. The plates were again washed and 100 lambda of p-nitrophenyl disodium phosphate (1 mg per ml) in 10% diethylamine buffer pH 9.6 added to each well. The plates were incubated 1–2 hours at room temperature. Color changes were read by Dynatech Microplate Reader MR600. The tests were specific for each Ig class over a range of 2 ng per ml to 50 μg per ml.

C.8.b. Assay for HLA Antigen

The presence of HLA antigens was assayed by indirect immunofluorescent binding with W6/32 murine monoclonal antibody, which recognizes a framework determinant on all HLA-A, B & C antigens (Brodsky, F. M., et al, *Immunological Rev* 47:1 (1979)). Briefly, cells were incubated with W6/32 followed by staining with fluorescent goat anti-mouse IgG (Tago) and analysis on an Ortho Cytofluorograph System 50H cell sorter, all by procedures known in the art.

C.8.c. Radioimmunoassay

The presence of anti-VZV in the supernatants of the triomas was determined using radioimmunoassay (RIA) by the method of Arvin, A., et al, *J Clin Microbiol,* 12:367 (1980). Briefly, commercial VZV antigen (Flow Laboratories) was added to each well of a polyvinyl "U"-plate (Dynatech Co., Alexandria, Va.) and the plate allowed to dry overnight at room temperature. The wells were washed with PBS, filled with PBS containing 20% fetal calf serum, incubated for one hour at 37°, rewashed several times with PBS, and dried. Supernatants to be tested were added to two wells containing antigen and the plates were then incubated 1 hour at 37° and washed 3× with PBS containing 0.05% Tween 20. Goat anti-human IgG, specific for the Fc fraction (Tago, Burlingame, Calif.), labeled with I(125) by a modified chloramine T method, was diluted to contain $2 \times 10^5$ cpm per ml and 250 lambda of this solution was added to each well. The plates were incubated for one hour at 37°, washed with cold PBS containing 0.05% Tween 20, and allowed to dry. The wells were separated by passing a hot wire below the surface of the plate, transferred to a counting vial and counted for one minute in a gamma scintillation counter (Beckman Instruments, Inc., Fullteron, Calif.). Controls used in each assay include known positive and negative sera and diluent alone. Specific antibody binding was considered to be present at each well for which the ratio of the mean cpm of the two wells containing supernatant and VZV antigen to mean cpm of the two wells containing serum and control antigen was greater than or equal to 2.5.

C.8.d VZV Viral Neutralization

VZV antibody was assessed by the plaque reduction multiplicity analysis. The assay is as described by Grose, et al, *J Infect Dis,* 139:432 (1979) using melanoma and VZV-32 obtained from him. Briefly, 200 lambda of a serial dilution of the partially purified human anti-VZV monoclonal antibody obtained by 45% ammonium sulfate preciptation of a serum free supernatant (HB101, Hana Biologic, Berkeley, Calif.) or murine monoclonal anti-VZV as a control was added to an equal volume of a stock cell-free VZV-32 to give a final concentration of 500 plaque forming units (pfu) per ml in IDMEM Gibco) without serum and incubated at 37° C. for 60 minutes, with intermittent shaking. After incubation, 200 lambda of the virus-antibody mix was inoculated into duplicate wells, in 24-well tissue culture plates (Costar, Cambridge, Mass.) containing a near confluent layer of melanoma cells which had been grown in IDMEM with 12.5% FCS supplemented with L-glutamine, non-essential amino acids, penicillin and gentamicin. Additionally, eight wells were inoculated with VZV-32 that had been diluted 1:1 (to yield 50 pfu/0.2 ml). The plates were incubated at 32° C. with intermittent shaking for 60 minutes. After suctioning off supernatants, the wells were filled with 1 ml of DMEM with 5% FCS and 0.75% carboxymethylcellulose (Sigma, St. Louis, Mo.). The plates were then incubated at 32° C., 5% $CO_2$ for seven to ten days. Subsequently, the wells were aspirated, and cells fixed and stained with crystal violet in 5% formaldehyde for three hours. After aspiration and overnight drying, plaques were counted with a dissecting microscope.

We claim:

1. An immortalizing fusion partner for use in producing a trioma cell line capable of secreting a human monoclonal antibody specific against a selected antigen, when fused with a non-malignant b-lymphoid cell derived from a human donor exposed to such antigen, comprising a fused mouse myeloma/non-malignant human B-lymphocyte cell line which (a) expresses HLA surface antigens, (b) does not secrete immunoglobulins, and (c) is deficient in hypoxanthine phosphoribosyl transferase, as evidenced by the inability of the cell line to grow in hypoxanthine-aminopterin-thymidine or azaserine-hypoxanthine medium.

2. The fusion partner of claim 1, which has the characteristics of ATCC HB 8464.

3. A trioma cell line capable of secreting a normal human monoclonal antibody specific against a selected antigen, said cell line comprising the fusion product of:
   (1) a mouse myeloma/non-malignant human B-lymphocyte hybridoma fusion partner which (a) expresses HLA surface antigens, (b) does not secrete immunoglobulins, and (c) is deficient in hypoxanthine phosphoribosyl transferase, as evidenced by the inability of the fusion partner to grow in hypoxanthine-aminopterin-thymidine or azaserine-hypoxanthine medium, and
   (2) a non-malignant B-lymphoid cell derived from a human donor exposed to the selected antigen.

4. The cell line of claim 3, for use in producing a monoclonal antibody which is immunoreactive with a microorganism known to cause acute infection in humans, wherein the B-lymphoid cell is derived from a human having such an acute infection.

5. The cell line of claim 4, for use in forming an antibody which is immunoreactive with varicella-zoster virus, wherein the B-lymphoid cell is derived from a human having an acute varicella zoster viral infection.

6. The cell line of claim 5, which has the characteristics of ATCC HB 8463.

7. The cell line of claim 3, wherein the lymphoid cell is stimulated in vitro under conditions which promote lymphoid cell growth in such medium, and the fusion partner is also resistant to a drug at a concentration which prevents growth of the stimulated lymphoid cell.

8. The cell line of claim 7, wherein the lymphoid cell is stimulated with Epstein-Barr virus, and the fusion partner is resistant to about 1 μM ouabain.

9. A method of producing a human monoclonal antibody which is specific against a selected antigen, comprising providing a fusion partner produced by fusing mouse myeloma cells and non-malignant human B-lymphocytes, selecting fusion products which show stable immunoglobulin secretion and HLA surface antigen production in culture, treating the selected fusion products with a mutagen, and selecting mutagenized fusion products which retain the ability to produce HLA surface antigen, show no immunoglobulin secretion, and are unable to survive in a growth medium which allows growth of a successful fusion product formed by fusing the fusion partner with a human immunoglobulin-secreting B-lymphoid cell, fusing the fusion partner with a non-malignant B-lymphoid cell derived from a human donor exposed to the selected antigen, and selecting fusion products which are viable in such medium and which secrete antigen-specific monoclonal antibody.

10. The method of claim 9, wherein the fusion partner has the characteristics of ATCC HB 8464.

11. The method of claim 9, for producing a monoclonal antibody which is immunoreactive against a microorganism known to cause acute infection in humans, wherein the B-lymphoid cells are derived from a human with said acute infection.

12. The method of claim 11, for producing a monoclonal antibody which is immunoreactive with varicella zoster virus antigen, wherein the B-lymphoid cells are derived from a human donor having an acute varicella zoster virus infection.

13. The method of claim: 12, wherein the antibody is made by a fusion product of the fusion partner and the B-lymphoid cells having the characteristics of ATCC HB 8463.

14. The method of claim 10, which further includes stimulating the human B-lymphoid cells in vitro prior to said fusing, and the fusion partner is also resistant to a drug at a concentration which prevents growth of the stimulated lymphocyte in said medium.

* * * * *